(12) United States Patent
Hanft et al.

(10) Patent No.: US 9,261,697 B2
(45) Date of Patent: *Feb. 16, 2016

(54) SCANNING DEVICE

(71) Applicant: Carl Zeiss Meditec AG, Jena (DE)

(72) Inventors: Marco Hanft, Hena (DE); Dirk Muehlhoff, Jena (DE); Mark Bischoff, Jena (DE); Mario Gerlach, Glienicke-Nordbahn (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/209,464

(22) Filed: Mar. 13, 2014

(65) Prior Publication Data

US 2014/0247472 A1  Sep. 4, 2014

Related U.S. Application Data

(63) Continuation of application No. 11/579,791, filed as application No. PCT/EP2006/002150 on Mar. 9, 2006, now Pat. No. 8,702,770.

(30) Foreign Application Priority Data

Mar. 26, 2005  (DE) ........................ 10 2005 013 9493

(51) Int. Cl.
*G02B 7/10* (2006.01)
*G02B 26/10* (2006.01)
*A61F 9/008* (2006.01)

(52) U.S. Cl.
CPC .............. *G02B 26/10* (2013.01); *A61F 9/0084* (2013.01); *G02B 7/10* (2013.01); *G02B 26/101* (2013.01); *A61F 2009/00872* (2013.01)

(58) Field of Classification Search
CPC ........... A61N 2005/067; A61N 5/0616; A61B 3/125; A61B 3/117

USPC .......... 359/368, 379, 389, 381; 351/200–221, 351/246; 607/88, 89
See application file for complete search history.

(56) References Cited

U.S. PATENT DOCUMENTS 3,703,176 A  11/1972  Vassiliadis et al.
4,554,141 A  11/1985  Scull et al.
(Continued)

FOREIGN PATENT DOCUMENTS

DE  196 19 481 C1  11/1997
DE  690 27 528 T2  8/1999
(Continued)

OTHER PUBLICATIONS

Merriam-Webster's Collegiate Dictionary p. 1258 (11$^{th}$ Ed. 2003).
(Continued)

*Primary Examiner* — Jennifer L. Doak
(74) *Attorney, Agent, or Firm* — Patterson Thuente Pedersen, P.A.

(57) ABSTRACT

The invention concerns a scanning device for focusing a beam of rays in defined regions of a defined volume, comprising an input optics wherein the beam of rays penetrates first, having at least one first optical element; a focusing optics for focusing the beam of rays exiting from the input optics; and a deflecting device arranged between the first optical element and the focusing optics, for deflecting the beam of rays after it has passed through the first optical element, based on a position of the focus to be adjusted in lateral direction. In order to adjust the position of the focus of the beam of rays in the direction of the beam of rays, and optical element of the input optics can be displaced relative to the deflecting device.

20 Claims, 3 Drawing Sheets

(56) References Cited

U.S. PATENT DOCUMENTS

| | | |
|---|---|---|
| 4,558,698 A | 12/1985 | O'Dell |
| 5,549,632 A | 8/1996 | Lai |
| 5,997,141 A | 12/1999 | Heacock |
| 6,094,300 A | 7/2000 | Kashima et al. |
| 6,235,014 B1 | 5/2001 | Abe et al. |
| 6,261,220 B1 | 7/2001 | Frey et al. |
| 6,524,330 B1 | 2/2003 | Khoobehi et al. |
| 6,626,895 B2 | 9/2003 | Frey et al. |
| 6,657,765 B2 | 12/2003 | Hayashi et al. |
| 6,676,655 B2 | 1/2004 | McDaniel |
| 6,751,033 B2 | 6/2004 | Goldstein et al. |
| 2003/0053219 A1 | 3/2003 | Manzi |
| 2004/0036936 A1 | 2/2004 | Nakajima et al. |
| 2004/0243112 A1 | 12/2004 | Bendett et al. |
| 2004/0254568 A1 | 12/2004 | Rathjen |
| 2005/0046936 A1 | 3/2005 | Dixon et al. |
| 2005/0096641 A1 | 5/2005 | Mizuno |
| 2006/0106371 A1 | 5/2006 | Muhlhoff et al. |
| 2008/0186551 A1 | 8/2008 | Hanft et al. |

FOREIGN PATENT DOCUMENTS

| | | |
|---|---|---|
| DE | 695 22 007 T2 | 4/2002 |
| DE | 103 23 422 A1 | 4/2004 |
| DE | 699 08 232 T2 | 4/2004 |
| DE | 10 2004 052 651 A1 | 5/2005 |
| EP | 0 654 984 B1 | 11/1998 |
| EP | 0 960 609 A1 | 12/1999 |
| GB | 1 512 037 | 5/1978 |
| WO | WO 03/068051 A2 | 8/2003 |
| WO | WO 2004/105661 A1 | 12/2004 |

OTHER PUBLICATIONS

Application and File History for U.S. Appl. No. 11/579,791, filed Nov. 7, 2006. Inventors: Hanft et al.

German Office Action for German Application No. 10 2005 013 949.3 dated May 12, 2015, 10 pages.

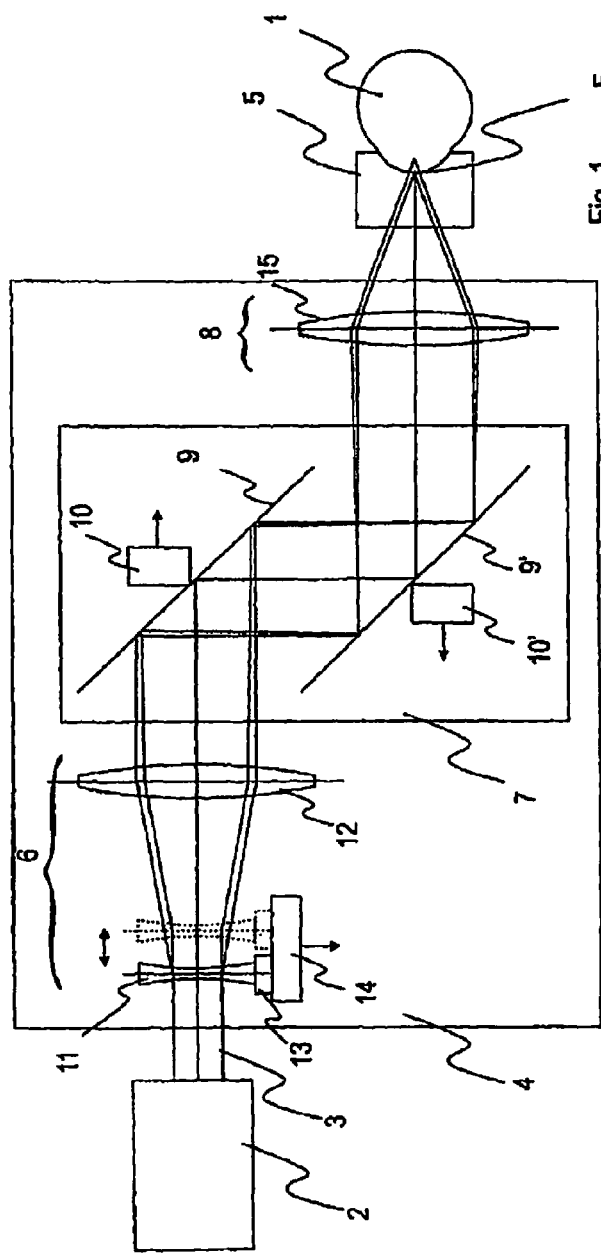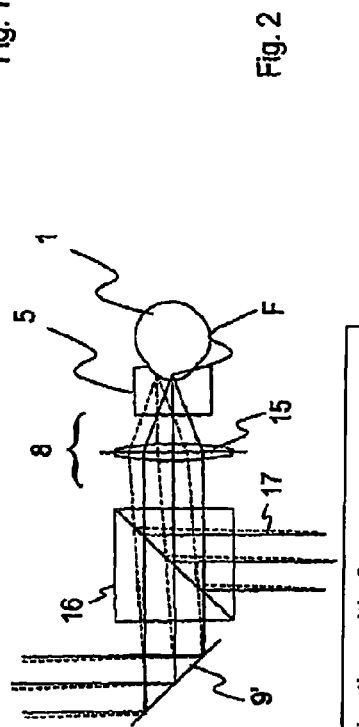

SCANNING DEVICE

RELATED APPLICATION

This application is a continuation of application Ser. No. 11/579,791, filed Nov. 7, 2006, entitled "Scan Device" which is a National Phase entry of PCT Application PCT/EP06/02150, filed Mar. 9, 2006, which claims priority to German Application No. 10 2005 013 9493, filed Mar. 26, 2005, each of which is hereby fully incorporated herein by reference.

FIELD OF THE INVENTION

The present invention concerns a scanning device for focusing a luminous beam in given ranges of a given volume, as well as a procedure for focusing a luminous beam into given ranges of a volume.

BACKGROUND OF THE INVENTION

The focusing of a luminous beam into different given ranges of a volume, this is both in a lateral and/or transversal direction to the luminous beam as well as in a parallel direction to the luminous beam, which plays an important role in a series of optical devices and/or with a set of optical procedures. From now on, as luminous beams must be conceived in particular laser beams delivered by a laser.

For example, laser beams are used in ophthalmology, in order to correct defective vision of a human eye by a laser-surgical intervention over the cornea of the eye. A special importance has the well-known procedure known as "LASIK" (laser in situ keratomileusis), in which by means of a pulsed laser beam material is removed not from the surface of the cornea, but from inside the cornea. This way, an external surface area of the cornea forms a fold-like cover also known as a "flap", whose thickness is substantially smaller than the one of the cornea. This cover is folded away for the actual removal treatment, whereupon a given amount of material is removed through the area of the opened region by means of a pulsed laser beam, with which the defective vision is corrected. Afterwards the cover is folded back on the opened surface.

In order to be able to cut the cover in the cornea to the exact defined depth as carefully and precisely as possible, femtosecond laser pulses may be used—this is, laser pulses with suggested pulse-widths lower than $10^{-12}$ s. By means of such pulses, optical openings—which are also denominated "photo-disruptions", which are locally limited and show an expansion of only a few micrometers—can be produced in the cornea. By placing several of these optical openings very close in exact given places, the cover can be formed very accurately. Thereby, a fundamental condition for the exact formation of the cover is the accurate positioning of the focus of the used pulsed laser beam, not only in the lateral direction, but most of all also in the depth of the cornea and thus in the propagation direction of the laser beam.

US 2003/0053219 A1 describes a zoom lens system which is intended for surgical applications. A zoom lens is moved in the direction of the laser beam for focusing into different depths, whereby the focal length of the focusing optics is modified. In order to be able to place the focus in the depth with the required accuracy, the zoom lens must be adjusted with a very high accuracy, which requires accordingly complex mechanics.

U.S. Pat. No. 6,751,033 B2 shows an ophthalmologic laser system, in which a laser beam delivered by a laser source is diverted in a lateral direction and thereafter is focused in a given depth by using optics with variable focal length. The same disadvantages of the system described in US 2003/0053219 A1 can be expected with this system.

A further application area for scanning devices of the above mentioned type are those denominated confocal laser scanning microscopes, in which a laser beam is focused on a given range of the volume of the object to be examined. The light emitted from this area is aimed over a detector in which a fine aperture is located over an intermediate image plane, which basically only allows the light emitted from the range and/or focus to pass, fading out the light from neighboring regions so that a dissolving takes place in the lateral and depth directions. A three-dimensional volume of the object which is being examined can be shown by the relative motion between specimen and focus in lateral direction and in the direction of the laser beam. The specimen table which holds the object is moved by positioning the focus in the direction of the laser beam relative to the object, is also mechanically complex and due to the relatively large mass of the sample table, does not allow a very fast adjustment.

The basic purpose of the concerned invention is to create a scanning device for focusing a luminous beam into determined ranges of a given volume by means of a simple laser beam, in a simple and exact way in the lateral direction and in the direction of the laser beam into different specific ranges of a volume, that can be focused following a determined procedure.

SUMMARY OF THE INVENTION

This purpose will be achieved by means of a scanning device for focusing a luminous beam into determined ranges of a given volume with a set of entrance optics, which the luminous beam enters first and which shows at least a first optical element and a focusing optics set, by means of which the luminous beam emitted by the entrance optics can be focused, and a deflecting device located between the first optical element and the focusing optics which will deflect the luminous beam in a lateral direction after passing through the first optical element depending on the focus position, so it can pass through or be reflected, and whereby at least one optical element of the entrance optics set can be moved relative to the deflecting device in the direction of the luminous beam, in order to adjust the focus position of the luminous beam.

The scanning device also adjusts in the direction of the luminous beam—which can be emitted from an optical radiation source such as a laser—in the direction of the entrance optics, which subordinate the deflecting device and finally the focusing optics. The entrance optics and the focusing optics cooperate in order to displace the focus position of the luminous beam in the direction of the luminous beam, whereby an optical element of the entrance optics, which can be in particular also the first optical element of the entrance optics, can be moved in the direction of the luminous beam relatively to the deflecting device and/or to the focusing optics, depending on the desired position of the focus.

The movement of the focus in lateral direction, for example transverse to the direction of the luminous beam, takes place via the deflecting device, which can be controlled in such a way by the control signals which are supplied for example by a suitable control device, that the focus can be moved in the lateral direction into a position either desired and/or determined by the control signals.

By placing the deflecting device between the first optical element—which preferably but not necessarily, can be in the beam direction of the first element of the entrance optics—and the focusing optics, the requirements of the entire optical system can be reduced since the entrance optics must only be placed for the beam near to the axis. This simplifies the correction and reduces the size of the elements. On the other hand, the focusing optics can be laid out in a simple way, since focusing takes place via the movement of an optical element of the entrance optics.

Altogether, a fast and simple adjustment of the three-dimensional focus position in the given volume can be achieved.

The divergence of the luminous beam emitted from the entrance optics is preferably modified by moving the displaceable optical element relative to the deflecting device. Such a configuration of the entrance optics has the advantage that the entrance optics can be built very simply. The focusing optics then focuses the luminous beam emitted from the entrance optics depending on its divergence angle on different depths—this is positions in the direction of the luminous beam in which a movement of the focusing optics is not necessary. Therefore the purpose of the invention is also further solved by a procedure for focusing a luminous beam into determined ranges of a volume, in which depending on the position of the corresponding regions, the divergence of the luminous beam is changed, and the luminous beam is transversally deflected to its direction of propagation and then focused. By changing the divergence of the luminous beam, it must be conceived that the convergence and/or divergence angle of the luminous beam will change, and that the luminous beams emitted by the scanning device can be convergent, divergent or preferably parallel. After changing the divergence and before the deflecting device, depending on the desired position of the focus, they can be divergent, parallel or convergent. The entrance optics and focusing optics are particularly and preferably laid out in such a way and arranged relatively to each other that a parallel luminous beam is transferred by the entrance optics again into a parallel luminous beam, if the focus is placed in the middle of the depth region of the predetermined volume. This has the advantage that it is possible to make corrections of the system, with which the aberrations with small focus penetration in the volume and the aberrations with large penetration can be mediated.

The first optical element of the entrance optics can be for example a lens, a reflective element such as a mirror, in particular a curved mirror or a hollow mirror, or a diffractive optical element. The optical element which can move relative to the deflecting device can be for example a lens. In another preferred application form, the movable optical element is a diffractive optical element that moves relative to the deflecting device.

Alternatively, it is preferred that the movable optical element that moves relative to the deflecting device is a reflective optical element.

In principle, the entrance optics can still show further optical elements beside the first optical element. The entrance optics may include a lens or a group of lenses with negative refraction power and a one of these lenses or group of lenses with positive refraction power may be arranged downstream in the direction of the luminous beam. Such an arrangement is characterized in a favorable way by a particularly compact structure, and contrary to an expander with two positive refraction power elements, shows no real intermediate image. The first optical element of the entrance optics can be in particular the negative refraction power lens or the first lens of the negative refraction power group of lenses. The lenses or groups of lenses can thereby be arranged in such a way that the entrance optics represents at least an expander for the position of the movable optical element that moves relative to the deflecting device, and by which the cross section of a parallel, incident luminous beam can be changed, especially increased. Such an arrangement is characterized in favorable way by a particularly compact structure.

In other implementation forms, instead of the negative refraction power lens or group of lenses and/or the positive refraction power lens or group of lenses, a similarly working diffractive optical element (DOE) and/or a group of diffractive optical elements or an similarly working reflective optical element and/or group of reflective optical elements can be used. The lenses or groups of lenses can be thus partially or completely replaced by diffractive optical elements or mirrors. The desired function of the divergence change is then achieved with other elements. Therefore in another application, a set of entrance optics with a first diffractive optical element arranged in the beam direction and a second diffractive optical element arranged in the beam direction can be used. In a basic arrangement, the first diffractive optical element transforms a parallel beam into a convergent beam, and the second diffractive optical element transforms the convergent beam again into a parallel beam, whereby as a result of the corresponding construction and arrangement of the diffractive optical elements, the beam expansion increases. By changing the divergence of the beam emitted from the entrance optics, the distance between the first and second diffractive optical elements is changed. As a further application, an entrance optics set with two concave mirrors is mentioned. The first concave mirror in the rays' path creates a real intermediate image, which is projected by the second mirror located in the path of rays from the first hollow mirror to infinity. The divergence is changed by changing the distance between the two concave mirrors. The focal length ratio determines the relationship between the diameter of the emitted beam and the diameter of the incoming beam. Also combinations of lenses, diffractive optical elements and mirrors can be used.

Preferably the optical element movable relative to the deflecting device is a negative refractive power lens or a negative refractive power group of lenses. In this case, the entrance optics set a particularly small number of components. In particular, the first optical element of the entrance optics can be movable relative to the optical element of the deflecting device. This entrance optics structure makes it possible on one hand to build the negative refraction power lens and the movable optical element with very small dimensions, which in consequence due to its small dimensions can move very fast. On the other hand, a particularly favorable speed ratio between the movement of the negative refraction power lens and the corresponding movement of the focus results in the direction of the luminous beam, this is that with an appropriate dimensioning of the entrance optics and the focusing optics, the movement of the negative refraction power lens entails a substantially smaller corresponding depth movement of the focus around a given distance, so that the accuracy requirements of a drive for the negative refraction power lens based on achieving a given precision of the adjustment of the focus position in the depth are relatively small.

In order to make possible a controlled movement of the movable optical element relative to the deflecting device, it may be mounted on a movable mounting plate parallel to the path of rays.

Preferably the scanning device must include a driving device for the relative movement of the movable optical element of the deflecting device. This can have, aside from the corresponding support of the movable optical element, yet another actuator which converts control signals from the corresponding motion. Some examples of this actuator can be a piezoactuator, an electrical linear motor or also an electric motor, whose rotational motion is converted into linear motion by a transmission, such as an eccentric cam drive so it can be used as actuator. When using electric motors, stepper motors may be used, which have the advantage that their movement can also be precisely controlled without regulation. Otherwise, the driving device can have an automatic control loop, which besides the actuator can also include a sensor for detecting the position of the movable optical element relative to the deflecting device and a controlling circuit, which controls the actuator depending on the position of the optical element detected by the sensor, so it can be moved to a determined target position.

The deflecting device can be in principle placed in any position between the first optical element of the entrance optics and the focusing optics. However, it is preferred that the deflecting device is arranged between the entrance optics and the focusing optics. This arrangement has the advantage that the entrance optics can be simply developed, since the luminous beam is not then moved in the entrance optics in lateral direction, if the luminous beam is moved by the deflecting device in a lateral direction.

The deflecting device can be, in principle, built in a well-known way. For example, it can work used for emitting the luminous beam over a reflective element, such as a mirror, in two different perpendicular axles, tiltable between each other, in which the deflecting device has at least one further actuator, by means of which the reflective element is tiltable around the two axes depending on the control signals. This application form has the advantage that only one reflective element is needed.

However, the deflecting device preferably may include two movable reflective elements separated from each other and from the focusing optics. Such a structure permits a very exact support and adjustment of the reflective elements and thus of the position of the focus in the lateral direction, this is in a transverse direction to the luminous beam close to its focus. The deflecting device can have in this case two further actuators, which convert in each case the control signals depending on the desired lateral diversion and/or position of the focus during the movement of the corresponding reflective element. In particular, the reflective elements for emitting the luminous beam are tiltable around axles, which are perpendicular to each other. At least one of the reflective elements can be a mirror.

The pupil optics may be arranged between the reflective elements, which image the first reflective element on the second reflective element. This arrangement has the advantage that a clear pupil position results, which in a particular case can be the reflective element that the luminous beam meets first and that works as a pupil. A clear and fixed position of the pupil is in fastidious—this is, very precisely working—optical systems a condition for a good correction.

In order to adjust the depth of the focus, this is in the direction of the luminous beam, the movable optical element designed according to the invention may move relative to the deflecting device. This does not exclude that the focusing optics have an adjustable focal length. It is however preferred that the focusing optics show a fixed focal length. In particular this does not include any zoom lens. With the procedure according to invention it is preferred that focusing optics with a fixed focal length is used for focusing the diverted luminous beam. The focusing optics is preferably arranged fixed relative to the deflecting device. With this application form the adjustment of the focus position is not made by changing the focusing optics, which has the advantage that this can be particularly simply laid out.

Preferably a beam splitter is arranged in the path of rays between the deflecting device and at least one emission lens or emission lenses group of the focusing optics. The focusing optics lens or group of lenses are located under the emission lens or emission lenses group of the focusing optics, from which the luminous beam is emitted into the volume on which it is to be focused. The beam splitter is thereby preferably arranged in such a way, that on one hand the luminous beams diverted from the deflecting device, fall on the emission lens or group of lenses, and on the other hand at least one part of an observation luminous beam from the path of rays between the deflecting device and the emission lens or emission lenses group, coming from the volume, is decoupled. Depending upon the wavelength of the radiation of the focusable scanning device luminous beam, the beam splitter can be laid out dichroitic, so that it affects the luminous beam and the observation luminous beam differently. Such scanning device has the advantage that the volume can be simply observed during the emission of the luminous beam using at least a part of the observation luminous beam coming from the volume. In particular, in the case that the focusing optics shows a fixed focal length and is arranged fixed and relative to the deflecting device, the volume can be observed independently of the focus position of the luminous beam with fixed adjusted optics or camera.

Preferably the emission lens or the emission lenses group is adjusted in such a way that a parallel luminous beam is focused into the given volume. The emission lens or emission lenses group can be conceived then as an objective lens or objective lenses group. Thereby preferably the emission lens or emission lenses group is laid out such that the entire volume is essentially imaged sharply to infinity, so that for monitoring the depth of field is so large that the entire volume can be shown and observed sharply without having to adjust the observation optics.

The focusing optics can be divided into partial optics. Preferably the focusing optics has an entrance objective for the production of a real intermediate image from the luminous beam delivering radiation source. The focusing optics can then preferably exhibit still another tubular optics, which images the intermediate image into the infinite. The intermediate image formed from the tubular optics infinity is then focused from the emission lens or group of lenses and/or emission optics into the target volume. The focusing optics can be more simply corrected by this multipart arrangement. Therefore compensation effects can be used between the different parts of the focusing optics and the tubular optics, for example the entrance objective. The partial optics can have larger focal lengths than the focusing optics altogether. Thus for example the ratio between the diameter of the incoming beam and the focal length of the entrance objective can be favorably arranged, facilitating the correction. Beyond that, a possible interface results for monitoring the parallel path of rays between the tubular optics and the emission optics. In particular the focal length of the emission lens or emission lenses group can be selected in such a way that monitoring is possible simply.

The scanning device can be used for an optical radiation sources, however preferably for lasers. In particular in this case it is preferred, that all real intermediate pictures emitted from the luminous beam radiation source are formed in a gaseous environment, in particular air or vacuum. This has the advantage that with the use of the scanning device, very high intensity laser radiations are not used in the optical openings in the optical components of the scanning device, such as lenses or mirrors, since it could damage them.

Preferably the entrance and focusing optics are chromatically corrected over the spectral range of selected femtosecond pulses that can be focused by passing through femtosecond pulses with a dispersion induced temporal broadening of less than about 30%. Preferably the entire optical system of the scanning device is corrected this way. The pulse duration can be obtained in the focus by an adapted dispersion management before the pulse enters the system and the already mentioned chromatic correction of the entire optical system, which is appropriate for less than 30% over the theoretically attainable pulse duration. Preferably this chromatic correction is appropriate for femtosecond pulses with wavelengths in a range of approx. 1040 nm. Such a scanning device is therefore suitable in particular for laser-surgical systems, which are meant for using femtosecond pulses for the formation of a cornea flap during a LASIK treatment.

Beyond that, the optical system is preferably corrected by limited diffraction, so that for example the aberration caused by the optics in the lateral direction is suppressed to a large extent and/or is reduced to a minimum.

The focusing optics is preferably regulated by an adjustment of at least 0.35. In particular during the use of the scanning device for laser-surgical purposes, it is preferred that the mobile optical element move relative to the deflecting device over a range sufficiently large that the focus of the luminous beam in the beam direction moves in a range larger than 0.5 mm. Such an adjustment has the advantage that when using the scanning device for a LASIK treatment, a cornea flap can be simply formed without movement of the cornea relative to the scanning device.

For the same purpose it is preferred that the deflecting device is adjusted in such a way that the focus of the luminous beam can move along the given volume in a lateral range with a diameter of about 11 mm. This again has the advantage that the necessary cornea covers can be formed with no movement of the cornea relative to the scanning device during the LASIK treatment.

The scanning device can be used with any sources of optical radiation, however showing preferably a femtosecond laser for the emission of femtosecond pulses along the luminous beam, whereby the laser which is laid over the entrance optics and the focusing optics of the focused luminous beam in the focus has a diameter smaller than 5 μm. Such scanning device is suitable in particular for the very precise preparation of the cornea cover during a LASIK treatment.

However, the scanning device can also be used for other purposes. Preferably a laser scanning microscope with a laser for emitting illumination laser radiation over a scanning device designed according to the invention for focusing the illumination laser radiation. The laser scanning microscope can have in particular control equipment, which is lead into the scanning device in such a way that the focus of the lighting laser radiation scans laterally and is directed into the depth by a given scanning volume. Preferably thereby a specimen holder of the laser scanning microscope and the focusing optics are at least arranged for scanning a sample fixed to each other. Such a laser scanning microscope has the advantage that it is not necessary to move the specimen table for moving the sample, which on one hand simplifies the structure substantially and on the other hand allows a faster adjustment of the focus position in the z-direction.

BRIEF DESCRIPTION OF THE DRAWINGS

The invention is described below in more detail using the drawings. They show:

FIG. 1 a schematic and simplified representation of a system for laser-surgical eye treatment with a scanning device designed according to an embodiment of the invention, FIG. 2 a schematic partial representation of a laser-surgical treatment system designed according to an embodiment of the invention, FIG. 3 a schematic representation of a system for the laser-surgical treatment of the eye with a scanning device designed according to an embodiment of the invention, and FIG. 4 a schematic representation of a laser scanning microscope designed according to an embodiment of the invention.

DETAILED DESCRIPTION OF THE DRAWINGS

Figure 3:
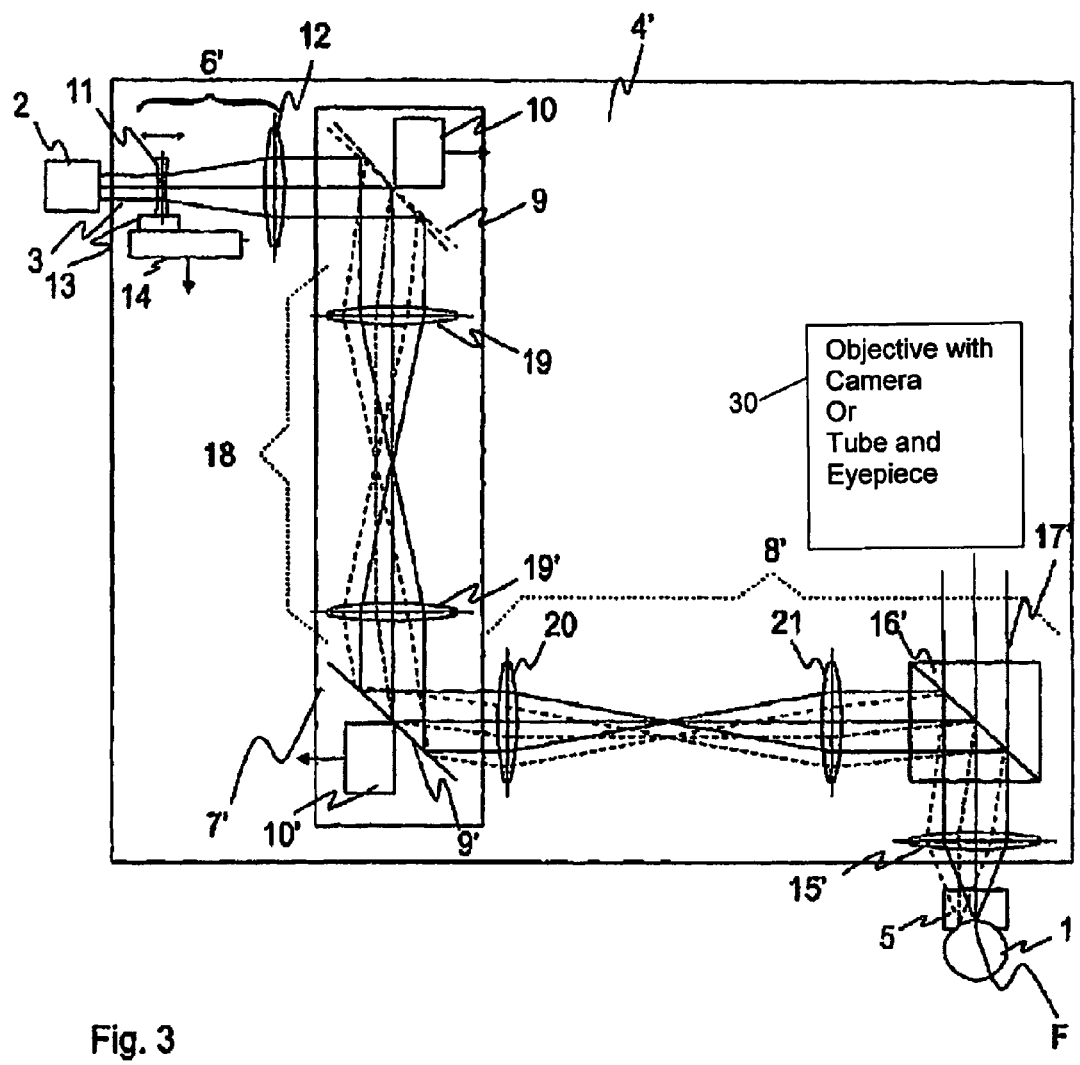

FIG. 1 shows a laser-surgical system for the treatment of a human eye 1 with a radiation source 2 in the form of a femtosecond laser for the emission of a pulsed laser radiation in the form of a pulsed luminous beam 3 and a scanning device 4 designed according to an embodiment of the invention, by means of which the luminous beam 3 can be focused into different, given ranges in a three-dimensional volume in the cornea of eye 1. On the cornea of eye 1 is a contact lens 5 with a concave contact area, against which rests the cornea of eye 1, whereby any movement of the cornea is suppressed during a treatment with laser radiation as much as possible.

The radiation source 2 in the form of a femtosecond laser is adjusted and actually prepared for the delivery of femtosecond pulses with a wavelength in a range of approx. 1040 Nm with a pulse width within the range of approximately 200 fs. It can in particular include pulse forming mechanisms beside the actual laser.

The scanning device 4 adjusts the direction of the luminous beam 3 over the entrance optics 6, by which the luminous beam 3 enters the scanning device 4, a deflecting device 7, the luminous beams 3 emitted from the laser from the entrance optics 6 corresponding to the given control signals in lateral direction, this is transverse to the direction of the luminous beams deflected from the deflecting device 7, and focusing optics 8 firmly arranged relative to the deflecting device 7, for focusing the luminous beam 3 emitted from the entrance optics 6 and diverted by the deflecting device 7, which focuses it in the region of the cornea of eye 1.

The deflecting device schematically shown 7 is adjusted in an actually known way and is regulated by two reflective elements 9 and 9' in the form of mirrors for the emission of the luminous beam 3, which can be tilted and supported on the axles not shown in FIG. 1. For a simpler representation, the reflective elements 9 and 9' are only shown parallel to each other in a schematic way, however the tilting axles run perpendicularly to each other and into a Z-axis of the entrance optics 6 in FIG. 1, so that by tilting the first reflective element 9 of luminous beam 3 in the Y-direction, this is in FIG. 1 upwards or downwards, and by tilting the second reflective element 9' in the Y-direction and the optical axis of the entrance optics perpendicularly in the X-direction, in FIG. 1 and/or from the indication level, can be diverted. The reflective elements and/or mirrors 9 and 9' are galvanometrically linked, whereby actuators 10 and/or 10' are intended to be connected with the control equipment in FIG. 1 by arrows that indicate signal connections. The control equipment gives correspondingly the desired focus position of luminous beam 3 in the lateral direction, this is in the x and y directions from the control signals from actuators 10 and 10', on which the reflective elements and/or mirrors 9 and 9' are tilted in a well-known way.

The entrance optics 6 is regulated over a movable optical element relative to the deflecting device 7 in the form of a first lens 11 with negative refraction power; this is a diverging lens, as first optical element as well as a collecting lens 12 which has positive refraction power. The Z-axis of these two lenses runs coaxially. The first lens 11 is placed in a lens holder 13, which is adjustable in a linear guide not shown in FIG. 1 in a parallel direction to the Z-axis of first lens 11, so that first lens 11 is an optical element of entrance optics 6 that can move relative to the deflecting device 7. The actuator only shown schematically in FIG. 1 serves for the movement of lens holder 13 and also to the first lens 11 parallel to their Z-axis, for example a linear drive 14 which is again indicated by an arrow, with which is connected to control equipment (not shown). This sends control signals to the linear drive 14 for the movement of the first lens 11 depending on the desired focus position along the direction of the luminous beam 3 within the range of the focus control signal. In this example, linear drive 14 is a stepper linear motor.

In a position of the movable optical element shown in FIG. 1 relative to the deflecting device 7 through lines drawn from first lens 11 to the collecting lens 12, the entrance optics 6 works as an expander that increases the cross section of luminous beam 3, whereby the parallel luminous beam 3 before the entrance optics 6 is made parallel again by these emitted luminous beam 3.

Focusing optics 8 is represented in FIG. 1 of this application example only as an stationary emission lens 15 relative to the deflecting device 7 and/or the objective lens in form of a collecting lens, which focuses the luminous beam 3 emitted from entrance optics 6 and diverted by deflecting device 7 in the lateral direction into the cornea region of eye 1. The emission lens 15 is however only a schematic representation of an optical system of positive refraction power, which may be more complex, and whereby this structure does not play a role in the context of this representation.

Focus position F of luminous beam 3 in the direction along the luminous beam is determined by entrance optics 6 and focusing optics 8. Focus position F in the direction of the luminous beam is adjusted by moving the first lens 11 along its Z-axis relative to deflecting device 7 and focusing optics 8. In case of a change of the distance between first lens 11 and collecting lens 12, the divergence of luminous beam 3 parallel to lens 11 is changed, which is clearly represented by the broken lines in FIG. 1. Depending on the position of the first lens 11, the luminous beams emitted from collecting lens 12 can be made parallel or convergent. Depending on the divergence, the fixed optics 8 focuses then the luminous beam into different distances from focusing optics 8 and/or the emitting lens 15.

In the following example, the first lens 11 can be moved very fast and simply, since with a diameter of approx. 6 mm it is small and light. Beyond that, the speed ratio of the movable optical element relative to deflecting device 7, this is the first lens 11, in a corresponding motion of focus F in the direction of luminous beam 3, in this example is for instance 20:1, which is substantially larger than the one used on the subordinate zoom optics of the deflecting device, with which typically a clearly smaller speed ratio can be expected. For example, in US 2003/0053219 A1 it has a value of 1:1.

FIG. 2 shows a laser-surgical system with a scanning device designed according to another embodiment of the invention. This scanning device differs from the first scanning device 4 as the path of rays between deflecting device 7 and focusing optics 8 is arranged with the collecting lens working as emission lens 15 and a beam splitter 16, by means of the outgoing observation luminous beams 17 from points in the cornea of eye 1, which approach infinity during the illustration of object points in the cornea of eye 1 by emitting lens 15, from the path of rays between deflecting device 7 and focusing optics 8 in the direction of a tube with eyepiece, not shown in the figures, or an objective with camera, not shown in the figures either, which can be at least partly diverted, so that it is possible to monitor the cornea during the emission of luminous beam 3 on that cornea. Therefore at least during the treatment duration, the focusing optics 8 and the cornea of eye 1 must keep a fixed relative distance between each other and the focal point of focusing optics 8 lies in the working volume, monitoring then also takes place with constant sharpness, if the focus of luminous beam 3 is moved into the depth, this is in a direction parallel to the direction of luminous beam 3 in the proximity of the focus. During the definition of the observation aperture, it is preferably considered that on one hand a sufficiently bright picture with good resolution and on the other hand a depth of field as large as possible can be achieved.

FIG. 3 shows partially and schematically a laser-surgical system with a scanning device 4' designed according to an embodiment of the invention. Those components which comply with the components of the first application example are designated with the same reference symbols and the applications in the first application example also apply here accordingly to these components.

The deflecting device 7 is replaced here by a deflecting device 7', which only differs from the deflecting device 7 by the distance of reflective elements 9 and 9' between each other. The tilting axle of reflective element 9 runs perpendicular to luminous beam 3 and cuts at least approximately the Z-axis of entrance optics 6. This correspondingly applies to reflective element 9' and focusing optics 8'. In the rest position, reflective elements 9 and 9' are aligned to each other in such a way that the incoming beam along the Z-axis of entrance optics 6 within the area of the tilting axle of the second reflective element 9' comes out through these. In the rest position, the mirrors are bent opposite the Z-axis of entrance optics 6 and/or focusing optics 8', for instance in an angle of 45°.

Beyond that, a pupil optics set 18 is arranged in the path of rays between reflective elements 9 and 9', which includes two collecting lenses 19 and 19', which image the luminous beam 3 emitted that first reaches reflective element 9 on the other reflective element 9', whereby a real intermediate image is formed in space, between the collecting lenses 19 and 19', in order to avoid optical openings in the components of the scanning device. In this way a fixed position of the pupil is achieved which facilitates a favorable implementation of focusing optics 8'. By the construction of reflective elements 9 and 9' into each other, the size of reflective element 9' can be kept small, as in the example the mirrors are shaped as ellipses, whose main and/or secondary axis have a length of approximately 21 mm and/or 15 mm.

Focusing optics 8' differs from the focusing optics 8 in several aspects. It is made out of multiple parts and has an entrance objective 20, which emits a luminous beam 3 which is laterally diverted from deflecting device 7' and a real intermediate image is focused on a Tubular lens 21, which shows the intermediate image depending on its position into infinity, a beam splitter 16' following tubular lens 21, which diverts the luminous beam 3 on the emission lens 15', and the emission lens 15' in which luminous beam 3 is here parallel or only weakly convergent or weakly divergent, then is focused depending on its fixed focal length on the cornea of eye 1 and thus functions as an objective lens.

The adjustment of the focus position in the lateral direction and in the direction of luminous beam 3 near the focus takes place as in the first application example.

The beam splitter 16' is adjusted in such a way that the observation luminous beams 17', which results from the points in the cornea of eye 1 imaged by emission lens 15' to infinity, by which beam splitters 16' are passed through a tube with an eyepiece not shown in FIG. 3, or through an objective with a camera, not shown in FIG. 3, can be supplied. As it is shown in the second application example, this makes it possible to monitor with the luminous beam 3 during a LASIK treatment.

The dismantling of the focusing optics in the entrance objective 20, in the tubular lens 21 and the emission lens 15' and/or the main objective has the advantage, asides from the possibility of making an interface possible for monitoring so that small beam diameters can be achieved at the entrance of the focusing optics. For example, the beam diameter can reach up to 15 mm, so that the reflective elements 9 and 9' can be used with a work diameter of 15 mm. This relatively small size of the reflective elements 9 and 9' is favorable for the achievement of high scanning speeds. Beyond that, the dismantling into subsystems makes possible a limited diffraction correction of the focusing optics for the focusing optics. Since the beams between the subsystems do not have to be corrected, compensation effects can be used, which clearly reduce the number of necessary lenses.

In order to avoid undesired reciprocal effects, all optical components are laid out in such a way in this as well as in all other application variations, that all real intermediate pictures are formed in the air and so also very intensive laser radiations cannot be directed towards the optical openings in the optical components.

The application examples described here are in each case an entire optical system of the scanning device, in particular the initial and focusing optics, for which the spectral width is chromatically corrected by using a femtosecond pulse. Pulse duration can be obtained by an adapted dispersion management before the pulse enters the system and the already mentioned chromatic correction of the entire optical system, whose focus dispersion is due to chromatic aberrations, lies less than 30% above the theoretically attainable pulse duration.

The movable optical element is movable over a distance relative to the deflecting device sufficiently large that the focus of the luminous beam can be moved in the beam direction over a range larger than about 0.5 millimeter. The deflecting device is further adjusted in such a way that the focus of the luminous beam can be moved in a lateral range which has a diameter of 11 mm.

The laser, the entrance optics and the focusing optics are laid out in such a way that the focused luminous beam in the focus has a diameter smaller than 5 micrometers. The focusing optics in the application example preferably has an opening larger than 0.35.

These laser-surgical systems are therefore suitable in particular for the formation of a hinged cornea flap by photo disruption by means of femtosecond pulses.

Figure 4:
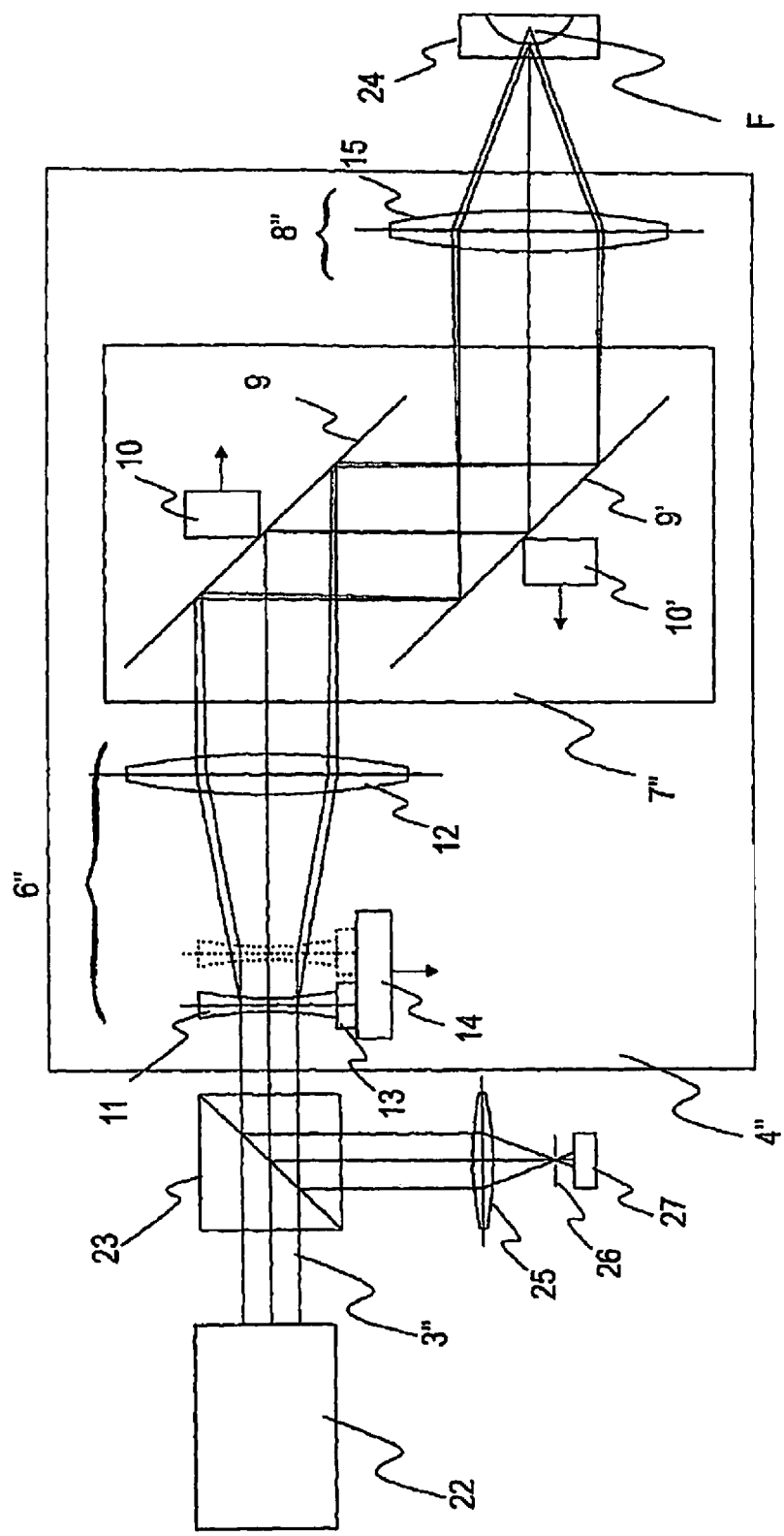

FIG. 4 shows a laser scanning microscope with a scanning device designed according to an embodiment of the invention.

From a radiation source 22, in the example a laser, a lighting luminous beam 3" is emitted, which arrives to a beam splitter 23 and then is lead into a scanning device 4", which is in principle built similar to the scanning device 4 of the first application example. However the dimensions of the used components on the application are adapted to a laser scanning microscope.

Scanning device 4" includes again an entrance optics 6", which changes the divergence of radiation beam 3" emitted from beam splitter 23 depending in the control signals received from the control equipment of the laser scanning microscope, not shown in FIG. 4, and a deflecting device 7", which diverts radiation beam 3" emitted from entrance optics 6" and which is laterally diverted depending on the control signals of the control equipment of the laser scanning microscope, and a firmly arranged focusing optics 8" relative to radiation beam 3" diverted by deflecting device 7", focused on the examined sample 24. The layout of the optical elements and the distances of entrance optics 6", deflecting device 7" and focusing optics 8" correspond to entrance optics 6, deflecting device 7 and focusing optics 8, so that the same reference symbols are used in FIG. 4 for these components and the explanations of these also apply accordingly here.

The radiation coming from sample 24 is focused again by focusing optics 8" and after passing deflecting device 7", entrance optics 6", as well as after being diverted by beam splitter 23, by collecting optics 25. The focus is blended with the focus of luminous beam 3" in sample 24. A fine aperture and/or pinhole screen 26 serves in a well-known way for depth discrimination, essentially by only letting through light from the focus of luminous beam 3". The optical radiation that passes through pinhole screen 26 is detected by a detection mechanism 27.

In order to generate an image, the control equipment not shown in the figures proceeds to rastering the focus of luminous beam 3" both transversally to the direction of luminous beam 3" and parallel to where the detected positions signals of the detection mechanism 27 are collected in each case. In addition, it delivers the appropriate control signals to deflecting device 7" and to linear drive 14 for the desired focus position in each case.

The size of the optical element which can be moved can also be kept here small and light with an appropriate adjustment of lens 11, so that a fast movement of the focus of luminous beam 3 relative to sample 24 can be achieved, so that the sample table on which sample 24 is held and which is not shown on FIG. 4 need not be moved.

A further application example differs from the second application example by adjusting the entrance optics. The lenses and/or groups of lenses are replaced here by diffractive optical elements. The entrance optics includes first and second diffractive optical elements. The first diffractive optical element is adjusted and arranged in such a way that it transforms a parallel beam in a basic position into a convergent beam. The second diffractive optic element following in the path of rays is adjusted and arranged in such a way that it again transfers the convergent beam into a parallel beam. All of this results altogether into an expansion of the beam. The distance between the first and second diffractive optical elements is modified for changing the divergence of the beam emitted from the entrance optics.

In another application example, the entrance optics of the preceding application example is changed in such a way that the entrance optics possesses now two concave mirrors, which are arranged in such a way that the distance between the laser and the deflecting device are doubled, resulting in an approach to the z-shaped path of rays. The first concave mirror produces a real intermediate image, which shows a subordinate suitable basic distance from the first concave mirror to the second concave mirror in the path of rays into infinity. The divergence is steered by changing the distance between the hollow mirrors. The focal length ratio determines the relationship between the diameter and/or the opening angles of the beam emitted from the entrance optics and the diameter and/or the opening angles of the incoming beam to the entrance optics.

REFERENCE SYMBOL LIST

1 Eye
2 Radiation source
3 3' Radiation beam
4 4' 4" Scanning device
5 Contact glass
6 6' Entrance optics
7 7' 7" Deflecting device
8 8' 8" Focusing optics
9 9' Reflective elements
10 10' Actuators
11 First lens
12 Collecting lens
13 Lens holder
14 Linear drive
15 15' Emission lens
16 16' Beam splitter
17 17' Observation luminous beam
18 Pupil optics
19 19' Collecting lenses
20 Entrance objective
21 Tubular lens
22 Radiation source
23 Beam splitter
24 Sample
25 Collecting optics
26 Pinhole screen
27 Detection device

The invention claimed is:

1. A surgical laser system including a scanning device for focusing a luminous beam into a selected range of an eye to be treated, the surgical laser system comprising:
   a femtosecond surgical laser source that produces the luminous beam, the femtosecond surgical laser source being structured to produce photo disruptions within tissues of an eye to be treated upon focal application of the luminous beam to the tissues;
   entrance optics following the femtosecond surgical laser source into which the luminous beam first enters comprising at least a first optical element, the first optical element comprising a lens or non planar mirror;
   focusing optics by which the luminous beam emitted from the entrance optics is focused on the eye to be treated;
   a deflecting device arranged between the first optical element and the focusing optics to divert a focus position of the luminous beam that leaves the first optical element in a lateral direction, the deflecting device comprising a first movable reflective element movable about a first axis configured to deflect the luminous beam in an X direction and a second movable reflective element movable about a second axis that is substantially orthogonal to the first axis configured to deflect the luminous beam in a Y direction;
   a beam splitter, located between the deflecting device and the focusing optics at a location where the luminous beam exhibits substantially parallel light rays, that directs observation beams from points in the cornea in a direction of a tube with an eye piece or an objective with a camera configured to permit monitoring of the cornea during application of the luminous beam to the cornea directly along an axis of the luminous beam as the luminous beam is applied to the cornea; and
   in which the entrance optics and focusing optics are chromatically corrected over a spectral range of selected femtosecond pulses, so that the femtosecond pulses can be focused with dispersion induced temporal broadening of less than about thirty percent.

2. The surgical laser system including a scanning device as claimed in claim 1, the entrance optics comprising at least one movable optical element that is configured to be movable along an axis generally parallel to the luminous beam where the luminous beam passes through the entrance optics to the deflecting device to adjust the focus position of the luminous beam within a portion of the eye.

3. The surgical laser system including a scanning device as claimed in claim 1, further comprising a contact lens following the deflecting device and the focusing optics that is engageable with a cornea of the eye, the contact lens having a contact area by which contact with the cornea is made.

4. The surgical laser system including a scanning device as claimed in claim 1, in which the at least one movable optical element, when displaced relative to the deflecting device, alters the divergence of the radiation beam emitted from the entrance optics.

5. The surgical laser system including a scanning device as claimed in claim 1, in which the first optical element of the entrance optics comprises a lens or a group of lenses with negative refractive power and further comprising a collecting lens or group of lenses with positive refractive power arranged in the direction of the luminous beam.

6. The surgical laser system including a scanning device as claimed in claim 1, in which the movable optical element comprises the first optical element and has a negative refraction power lens or comprises a group of lenses having negative refractive power.

7. The surgical laser system including a scanning device as claimed in claim 2, in which the movable optical element comprises a diffractive optical element.

8. The surgical laser system including a scanning device as claimed in claim 2, in which the movable optical element comprises a reflective optical element.

9. The surgical laser system including a scanning device as claimed in claim 2, further comprising a driving device which moves the movable optical element relative to the deflecting device.

10. The surgical laser system including a scanning device as claimed in claim 9, in which the driving device comprises a linear drive.

11. The surgical laser system including a scanning device as claimed in claim 1, in which the deflecting device is positioned between the entrance optics and the focusing optics.

12. The surgical laser system including a scanning device as claimed in claim 11, further comprising pupil optics, and a collecting lens which is arranged between the reflective elements, in which the first reflective element is imaged on the second reflective element.

13. The surgical laser system including a scanning device as claimed in claim 1, in which the focusing optics have a fixed focal length.

14. The surgical laser system including a scanning device as claimed in claim 1, wherein the focusing optics further comprises an emission lens or group of emission lenses and further comprising a beam splitter positioned in the path of rays between the deflecting device and the emission lens or the group of emission lenses of the focusing optics.

15. The surgical laser system including a scanning device as claimed in claim 14, in which the emission lens or the emission lens group focuses a substantially parallel luminous beam into the given volume.

16. The surgical laser system including a scanning device as claimed in claim 1, in which the focusing optics creates a real intermediate image through an entrance objective, produced by the luminous beam emitted from a radiation source.

17. The surgical laser system including a scanning device as claimed in claim 1, in which all real intermediate images produced by the luminous beam emitted by the femtosecond surgical laser source are formed in gas, air or vacuum.

18. The surgical laser system including a scanning device as claimed in claim 1, in which the movable optical element is movable over a distance relative to the deflecting device sufficiently large that the focus of the luminous beam can be moved in the beam direction over a range larger than about 0.5 millimeter.

19. The surgical laser system including a scanning device as claimed in claim 1, in which the deflecting device is operable such that the focus of the luminous beam can be moved laterally in a range having a diameter of at least about eleven millimeters.

20. The surgical laser system including a scanning device as claimed in claim 1, further comprising a femtosecond laser radiation source that emits femtosecond laser pulses along the luminous beam and in which the radiation source, the entrance optics and the focusing optics are configured such that the focus of the luminous beam has a diameter smaller than about five micrometers.

* * * * *

UNITED STATES PATENT AND TRADEMARK OFFICE
CERTIFICATE OF CORRECTION

PATENT NO. : 9,261,697 B2
APPLICATION NO. : 14/209464
DATED : February 16, 2016
INVENTOR(S) : Marco Hanft et al.

Page 1 of 2

It is certified that error appears in the above-identified patent and that said Letters Patent is hereby corrected as shown below:

ON THE TITLE PAGE

Item 72, in the Inventors:
In line 1, delete "Hena" and insert --Jena--

Item 57, in the Abstract:
In line 11, delete "and" and insert --an--

IN THE SPECIFICATION

Column 1, Line 26:
Delete "as"

Column 2, Line 16:
Insert a --,-- after "table" and insert a --,-- after "object"

Column 3, Line 55:
Delete "a"

Column 4, Line 1:
Delete the first ","

Column 5, Line 4:
Insert --an-- after "as"

Column 5, Line 24:
Delete "used"

Signed and Sealed this
Twenty-fourth Day of May, 2016

Michelle K. Lee
*Director of the United States Patent and Trademark Office*

CERTIFICATE OF CORRECTION (continued)
U.S. Pat. No. 9,261,697 B2

IN THE SPECIFICATION

Column 5, Line 26:
Delete "axles" and insert --axes--

Column 5, Line 51:
Insert --In demanding optical systems, that is very precise optical systems,-- after "pupil."

Column 5, Line 51:
Delete "A" and insert --a--

Column 5, Line 52:
Delete "in fastidious—this is, very precisely working—optical systems"

Column 9, Line 28:
Delete "an" and insert --a--

Column 11, Line 16:
Delete "asides" and insert --aside--

Column 12, Line 34:
Delete "positions" and insert --position--